(12) United States Patent
Kossmann et al.

(10) Patent No.: US 6,686,514 B2
(45) Date of Patent: *Feb. 3, 2004

(54) NUCLEIC ACID MOLECULES ENCODING STARCH PHOSPHORYLASE FROM MAIZE

(75) Inventors: Jens Kossmann, Berlin (DE); Claus Frohberg, Berlin (DE)

(73) Assignee: PlantTec Biotechnologie GmbH Forshung & Entwicklung (DE)

( * ) Notice: Subject to any disclaimer, the term of this patent is extended or adjusted under 35 U.S.C. 154(b) by 13 days.

This patent is subject to a terminal disclaimer.

(21) Appl. No.: 10/047,757

(22) Filed: Jan. 14, 2002

(65) Prior Publication Data

US 2002/0133849 A1 Sep. 19, 2002

Related U.S. Application Data

(62) Division of application No. 09/394,200, filed on Sep. 10, 1999, now Pat. No. 6,353,154, which is a continuation of application No. PCT/EP98/01183, filed on Mar. 3, 1998.

(30) Foreign Application Priority Data

Mar. 10, 1997 (DE) .......................................... 197 09 775

(51) Int. Cl.$^7$ ........................ C12N 15/29; C12N 15/54; C12N 15/82; A01H 5/00; C12P 19/00
(52) U.S. Cl. ...................... 800/284; 800/278; 800/286; 800/317.2; 800/320; 800/320.1; 800/320.2; 800/320.3; 536/23.6; 536/24.5; 435/101; 435/194; 435/320.1; 435/412; 435/419; 435/468
(58) Field of Search ............................. 536/23.6, 24.5; 435/101, 194, 320.1, 412, 419, 468; 820/278, 284, 286, 317.2, 320, 320.1, 320.2, 320.3

(56) References Cited

U.S. PATENT DOCUMENTS

| | | | |
|---|---|---|---|
| 5,824,790 A | 10/1998 | Keeling et al. | ............ 536/23.6 |
| 5,998,701 A | 12/1999 | Kawchuk et al. | ........... 800/284 |

FOREIGN PATENT DOCUMENTS

| | | |
|---|---|---|
| WO | WO 94/28149 | 12/1994 |
| WO | WO 95/07355 | 3/1995 |
| WO | WO 95/34660 | 12/1995 |
| WO | WO 96/12812 | 5/1996 |
| WO | WO 97/44471 | 11/1997 |

OTHER PUBLICATIONS

P. Buchner et al., "Glucan Phosphorylases in *Vicia faba* L.: Cloning, Structural Analysis and Expression Patterns of Cytosolic and Plastidic Forms in Relation to Starch,"*Planta* 199, 64–73 (1996).

E. Duwenig et al., "The Role of Starch Phosphorylase in Potato: The Functional Analysis of an Enigmatic Enzyme," *Plant Physiology Supplement* 111, 48 (1996).

E. Duwenig et al., "Induction of Genes Encoding Plastidic Phosphorylase from Spinach (*Spinacia oleracea* L.) and Potato (*Solanum tuberosum* L.) by Exogenously Supplied Carbohydrates in Excised Leaf Discs," *Planta* 203, 111–120 (1997).

J. Kossmann et al., "Transgenic Plants as a Tool to Understand Starch Biosynthesis," *Progress in Biotechnol.* 10, 271–278 (1995).

C. Lin et al., "Primary Structure of Sweet Potato Starch Phosphorylase Deduced from its cDNA Sequence," *Plant Physiol.*95, 1250–1253 (1991).

C.–T. Lin et al., "The Gene Structure of Starch Phosphorylase from Sweet Potato," Accession No. L25626, EMBL Sequence Data Library (1993).

C–T. Lin et al., "The Gene Structure of Starch Phosphorylase from Sweet Potato," *Plant Physiology* 107, 277–278 (1995).

H. Mori et al., "Potato Tuber Type H Phosphorylase Isozyme," *The Journal of Biological Chemistry* 266, 18446–18453 (1991).

K. Nakano et al., "Molecular Cloning of cDNA Encoding Potato Amyloplast α–Glucan Phosphorylase and the Structure of Its Transit Peptide," *J. Biochem.*106, 691–695 (1989).

U. Sonnewald et al., "A Second L–Type Isozyme of Potato Glucan Phosphorylase: Cloning Antisense Inhibition and Expression Analysis," Accession No. X73684, EMBL Sequence Data Library (1993).

U. Sonnewald et al., "A Second L–Type Isozyme of Potato Glucan Phosphorylase: Cloning, Antisense Inhibition and Expression Analysis," *Plant Molecular Biology* 27, 567–576 (1995).

B. St. Pierre et al., "The Starch Phosphorylase Gene is Subjected to Different Modes of Regulation in Starch–Containing Tissues of Potato," *Plant Molecular Biology* 30, 1087–1098 (1996).

C.–Y. Tsai et al., "Starch–Deficient Maize Mutant Lacking Adenosine Diphosphate Glucose Pyrophosphorylase Activity," *Science* 151, 341–343 (1966).

*Primary Examiner*—David T. Fox
(74) *Attorney, Agent, or Firm*—Fish & Neave; James F. Haley, Jr.; Grant Kalinowski

(57) ABSTRACT

Nucleic acid molecules are described which encode enzymes involved in the starch synthesis in plants. These enzymes are starch phosphorylases from maize. The invention further relates to vectors containing such nucleic acid molecules and to host cells transformed with the described nucleic acid molecules, in particular to transformed plant cells and to plants which may be regenerated therefrom and which exhibit an increased or reduced activity of the described proteins.

14 Claims, 1 Drawing Sheet

NUCLEIC ACID MOLECULES ENCODING STARCH PHOSPHORYLASE FROM MAIZE

This application is a divisional of U.S. application Ser. No. 09/394,200, filed Sep. 10, 1999, now U.S. Pat. No. 6,353,154, which is a continuation of PCT/EP98/01183, filed Mar. 3, 1998.

FIELD OF THE INVENTION

The present invention relates to nucleic acid molecules encoding a starch phosphorylase from maize. Furthermore, the present invention relates to vectors, bacteria as well as to plant cells transformed with the described nucleic acid molecules and to the plants containing the same. Moreover, methods for the production of transgenic plants are described which, due to the introduction of DNA molecules encoding a starch phosphorylase from maize, synthesize a starch which is modified in its properties.

With respect to the increasing significance which has recently been ascribed to vegetal substances as regenerative sources of raw materials, one of the objects of biotechnological research is to try to adapt vegetal raw materials to the demands of the processing industry. In order to enable the use of regenerative raw materials in as many areas as possible, it is furthermore important to obtain a large variety of substances.

Apart from oils, fats and proteins, polysaccharides constitute the essential regenerative raw materials derived from plants. Apart from cellulose, starch maintains an important position among the polysaccharides, being one of the most significant storage substances in higher plants. Among those, maize is one of the most interesting plants as it is the most important cultivated plant for the production of starch.

The polysaccharide starch is a polymer made up of chemically homogeneous basic components, namely the glucose molecules. However, it constitutes a highly complex mixture from various types of molecules which differ from each other in their degree of polymerization and in the degree of branching of the glucose chains. Therefore, starch is not a homogeneous raw material. One differentiates particularly between amylose-starch, a basically non-branched polymer made up of α-1,4-glycosidically branched glucose molecules, and amylopectin-starch which in turn is a complex mixture of various branched glucose chains. The branching results from additional α-1,6-glycosidic interlinkings. In plants used typically for the production of starch, such as maize or potato, the synthesized starch consists of approximately 25% amylose-starch and of about 75% amylopectin-starch.

In order to enable as wide a use of starch as possible, it seems to be desirable that plants be provided which are capable of synthesizing modified starch which is particularly suitable for various uses. One possibility to provide such plants—apart from breeding methods—is the specific genetic modification of the starch metabolism of starch-producing plants by means of recombinant DNA techniques. However, a prerequisite therefore is to identify and to characterize the enzymes involved in the starch synthesis and/or the starch modification as well as to isolate the respective DNA molecules encoding these enzymes.

The biochemical pathways which lead to the production of starch are basically known. The starch synthesis in plant cells takes place in the plastids. In photosynthetically active tissues these are the chloroplasts, in photosynthetically inactive, starch-storing tissues the amyloplasts.

The most important enzymes involved in starch synthesis are starch synthases as well as branching enzymes. In the case of other enzymes and also, for example, in the case of starch phosphorylases, their precise role during starch biosynthesis is unknown.

In order to provide further possibilities in order to modify starch-storing plants in such a way that they synthesize a modified starch, it is necessary to identify DNA sequences encoding further enzymes involved in the starch biosynthesis, such as starch phosphorylase. Such proteins are known, for example, from *Vicia faber* (Buchner et al., Planta 199 (1996), 64–73), *Solanum tuberosum* (St. Pierre and Brisson, Plant Science 110 (1995), 193–203; Sonnewald et al., Plant. Mol. Biol. 27 (1995), 567–576; Bhatt and Knowler, J. Exp. Botany 41 (Suppl.) (1990), 5–7; Camirand et al., Plant Physiol. 89 (4 Suppl.) (1989), 61), *Ipomoea batatas* (Lin et al., Plant Physiol. 95 (1991), 1250–1253), sugar beet (Li et al., Ohio J. of Sci. 90 (1990), 8), spinache and maize (Mateyka and Schnarrenberger, Plant Physiol. 86 (1988), 417–422) as well as pea (Conrads et al., Biochim. Biophys. Acta 882 (1986), 452–464).

They are characterized as enzymes catalyzing the reversible phosphorylysis of terminal glucose units of α-1,4-glucans according to the following equation:

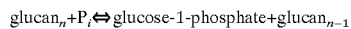

$$\text{glucan}_n + P_i \Leftrightarrow \text{glucose-1-phosphate} + \text{glucan}_{n-1}$$

Depending on the relative concentration of $P_i$ and glucose-1-phosphate (G1P), the enzyme may have a degrading or, as the case may be, synthesizing effect on the glucans (Waldmann et al., Carbohydrate Research 157 (1986), C4–C7). On the basis of the differences in the localization, in the affinities to the glucans and in the regulation and the size of monomers, the plant starch phosphorylases are classified as follows:

Type 1: situated within the cytosol of plant cells; very high affinity to longer-chained branched glucans; unregulated; monomeric size of approximately 90 kD;

Type 2: situated within the plastids of plant cells; affinity to maltodextrines; low affinity to polyglucans; unregulated; monomeric size of approximately 105 kD.

DNA sequences encoding the corresponding starch phosphorylases have so far been isolated only from a small number of plant species such as potato (Buchner et al., loc. cit.; Sonnewald et al., loc. cit.; Bhatt and Knowler, loc. cit.; Camirand et al., loc. cit.), sweet potato (Lin et al., loc. cit., Lin et al., Plant Physiol. 95 (1991), 1250–1253) and rice (database accession number DDBJ No. D23280). Up to now, such sequences are not known from maize.

Therefore, it is the object of the present invention to provide further nucleic acid molecules encoding enzymes involved in starch biosynthesis and by means of which genetically modified plants may be produced that show an elevated or reduced activity of those enzymes, thereby prompting a modification in the chemical and/or physical properties of the starch synthesized in these plants.

This object is achieved by the provision of the embodiments described in the claims.

SUMMARY OF THE INVENTION

Therefore, the present invention relates to nucleic acid molecules encoding proteins with the biological activity of a starch phosphorylase from maize, wherein such molecules preferably encode proteins which comprise the amino acid sequence depicted under Seq ID No. 2. The invention particularly relates to nucleic acid molecules which comprise all or part of the nucleotide sequence mentioned under Seq ID No. 1, preferably molecules, which comprise the coding region indicated in Seq ID No. 1 or, as the case may be, corresponding ribonucleotide sequences.

The present invention further relates to nucleic acid molecules which encode a starch phosphorylase from maize and one strand of which hybridizes to one of the above-mentioned molecules. Nucleic acid molecules that encode a starch phosphorylase from maize and the sequence of which differs from the nucleotide sequences of the above-mentioned molecules due to the degeneracy of the genetic code are also the subject-matter of the invention.

The invention also relates to nucleic acid molecules showing a sequence which is complementary to the whole or to a part of one of the above-mentioned sequences.

In this invention the term "hybridization" signifies hybridization under conventional hybridizing conditions, preferably under stringent conditions as described for example in Sambrook et al., Molecular Cloning, A Laboratory Manual, 2nd Edition (1989) Cold Spring Harbor Laboratory Press, Cold Spring Harbor, N.Y.). "Hybridization" preferably means that a hybridization takes place under the following conditions:

Hybridization buffer: 2×SSC; 10×Denhardt's solution (Fikoll 400+PEG+BSA; ratio 1:1:1); 0.1% SDS; 5 mM EDTA; 50 mM $Na_2HPO_4$; 250 μg/ml herring sperm DNA; 50 μg/ml tRNA; or 0.25 M sodium phosphate buffer pH 7.2; 1 mM EDTA; 7% SDS Hybridization temperature T=65 to 68° C.

Washing buffer: 0.2×SSC; 0.1% SDS

Washing temperature: T=40 to 68° C.

Nucleic acid molecules hybridizing to the molecules of the invention may principally encode starch phosphorylases from any desired maize plant expressing such proteins.

Nucleic acid molecules hybridizing to the molecules according to the invention may be isolated e.g. from genomic or from cDNA libraries produced from maize plants or maize tissue. Alternatively, they may have been produced by means of recombinant DNA techniques or by means of chemical synthesis. The identification and isolation of such nucleic acid molecules may take place by using the molecules according to the invention or parts of these molecules or, as the case may be, the reverse complement strands of these molecules, e.g. by hybridization according to standard methods (see e.g. Sambrook et al., 1989, Molecular Cloning, A Laboratory Manual, 2nd Edition, Cold Spring Harbor Laboratory Press, Cold Spring Harbor, N.Y.).

As a probe for hybridization e.g. nucleic acid molecules may be used which exactly or basically contain the nucleotide sequences indicated under Seq ID No. 1 or parts thereof. The fragments used as hybridization probe may also be synthetic fragments which were produced by means of the conventional synthesizing methods and the sequence of which is basically identical with that of a nucleic acid molecule according to the invention.

The molecules hybridizing to the nucleic acid molecules of the invention also comprise fragments, derivatives and allelic variants of the above-described nucleic acid molecules which encode a starch phosphorylase from maize as described in the invention. In this context, fragments are defined as parts of the nucleic acid molecules, which are long enough in order to encode one of the described proteins. In this context, the term derivatives means that the sequences of these molecules differ from the sequences of the above-mentioned nucleic acid molecules at one or more positions and that they exhibit a high degree of homology to these sequences. Homology means a sequence identity of at least 40%, in particular an identity of at least 60%, preferably of more than 80% and still more preferably a sequence identity of more than 90%. The deviations occurring when comparing with the above-described nucleic acid molecules might have been caused by deletion, substitution, insertion or recombination.

Moreover, homology means that functional and/or structural equivalence exists between the respective nucleic acid molecules or the proteins they encode. The nucleic acid molecules, which are homologous to the above-described molecules and represent derivatives of these molecules, are generally variations of these molecules, that constitute modifications which exert the same biological function. These variations may be naturally occurring variations, for example sequences derived from other maize varieties, or mutations, whereby these mutations may have occurred naturally or they may have been introduced by means of a specific mutagenesis. Moreover the variations may be synthetically produced sequences. The allelic variants may be naturally occurring as well as synthetically produced variants or variants produced by recombinant DNA techniques.

The proteins encoded by the various variants of the nucleic acid molecules according to the invention exhibit certain common characteristics. Enzyme activity, molecular weight, immunologic reactivity, conformation etc. may belong to these characteristics as well as physical properties such as the mobility in gel electrophoresis, chromatographic characteristics, sedimentation coefficients, solubility, spectroscopic properties, stability, pH-optimum, temperature-optimum etc.

The enzymatic properties of starch phosphorylases were described above. The localization and the acitivity of the phosphorylase may be assessed as described, for example, in Setup and Latzko (Planta 145 (1979), 69–75). The monomeric size may be determined by methods known to the skilled person.

The nucleic acid molecules of the invention may be DNA molecules, particularly cDNA or genomic molecules. The nucleic acid molecules of the invention may furthermore be RNA molecules. The nucleic acid molecules of the invention may, e.g. be derived from natural sources or produced by recombinant DNA techniques or synthetically.

Oligonucleotides hybridizing specifically to one of the nucleic acid molecules of the invention are also subject-matter of the invention. Such oligonucleotides preferably have a length of at least 10, particularly of at least 15 and still more preferably have a length of at least 50 nucleotides. They are characterized in that they hybridize specifically to the nucleic acid molecules of the invention, i.e. they do not or only to a small extent hybridize to nucleic acid sequences encoding other proteins, particularly other starch phosphorylases. The oligonucleotides of the invention may be used for example as primers for a PCR or as a hybridization probe for isolating related genes. They may also be components of antisense-constructs or DNA molecules encoding suitable ribozymes.

Furthermore, the invention relates to vectors, especially plasmids, cosmids, viruses, bacteriophages and other vectors common in genetic engineering, which contain the above-mentioned nucleic acid molecules of the invention. Such vectors are preferably vectors which can be used used for the transformation of plant cells. More preferably, they allow for the integration of the nucleic acid molecules of the invention into the genome of the plant cell, if necessary in combination with flanking regulatory regions. Examples are binary vectors which may be used in the Agrobacterium-mediated gene transfer.

In a preferred embodiment the nucleic acid molecules contained in the vectors are linked to regulatory elements that ensure the transcription and synthesis of a translatable RNA in procaryotic or eucaryotic cells.

The expression of the nucleic acid molecules of the invention in procaryotic cells, e.g. in *Escherichia coli*, is interesting insofar as this enables a more precise characterization of the enzymatic activities of the enzymes encoded by these molecules. In particular, it is possible to characterize the product being synthesized by the respective enzymes in the absence of other enzymes which are involved in the starch synthesis of the plant cell. This makes it Possible to draw conclusions about the function, which the respective protein exerts during the starch synthesis within the plant cell.

Moreover, it is possible to introduce various mutations into the nucleic acid molecules of the invention by means of conventional molecular-biological techniques (see e.g. Sambrook et al., 1989, Molecular Cloning, A Laboratory Manual, 2nd Edition, Cold Spring Harbor Laboratory Press, Cold Spring Harbor, N.Y.), which leads to the synthesis of proteins with possibly modified biological properties. By means of this it is on the one hand possible to produce deletion mutants, in which nucleic acid molecules are produced by continuing deletions at the 5'- or the 3'-end of the encoding DNA-sequence. These nucleic acid molecules may lead to the synthesis of correspondingly shortened proteins. Such deletions at the 5'-end of the nucleotide sequence make it possible, for example, to identify amino acid sequences which are responsible for the translocation of the enzyme in the plastids (transit peptides). This allows for the specific production of enzymes which due to the removal of the respective sequences are no longer located in the plastids but within the cytosol, or which due to the addition of other signal sequences are located in other compartments.

On the other hand point mutations may also be introduced at positions where a modification of the amino acid sequence influences, for example, the enzyme activity or the regulation of the enzyme. In this way e.g. mutants with a modified $K_m$-value may be produced, or mutants which are no longer subject to the regulation mechanisms by allosteric regulation or covalent modification usually occurring in cells.

Furthermore, mutants may be produced exhibiting a modified substrate or product specificity. Moreover, mutants with a modified activity-temperature-profile may be produced.

For the genetic manipulation in procaryotic cells the nucleic acid molecules of the invention or parts of these molecules may be integrated into plasmids which allow for a mutagenesis or a sequence modification by recombination of DNA sequences. By means of standard methods (cf. Sambrook et al., 1989, Molecular Cloning: A laboratory manual, 2nd edition, Cold Spring Harbor Laboratory Press, N.Y., USA) base exchanges may be carried out or natural or synthetic sequences may be added. In order to connect the DNA fragments, adapters or linkers may be attached to the fragments. Moreover, use can be made of manipulations which offer suitable restriction sites or which remove superfluous DNA or restriction sites. Wherever use is made of insertions, deletions or substitutions, in vitro mutagenesis, "primer repair", restriction or ligation may be used. For analyzing use is usually made of a sequence analysis, a restriction analysis or further biochemico-molecularbiological methods.

In a further embodiment the invention relates to host cells, in particular procaryotic or eucaryotic cells, which have been transformed by an above-mentioned nucleic acid molecule of the invention or by a vector of the invention, as well as cells derived from cells transformed in such a way and containing a nucleic acid molecule of the invention or a vector of the invention. This is preferably a bacterial cell or a plant cell.

Furthermore, the proteins encoded by the nucleic acid molecules of the invention are the subject-matter of the invention as well as methods for their production in which a host cell of the invention is cultivated under conditions that allow for the synthesis of the protein and in which the protein is subsequently isolated from the cultivated cells and/or the culture medium.

By making available the nucleic acid molecules of the invention it is now possible—by means of recombinant DNA techniques—to interfere with the starch metabolism of plants in a way so far impossible. Thereby, the starch metabolism may be modified in such a way that a modified starch is synthesized which e.g. is modified, compared to the starch synthesized in wildtype plants, with respect to its physico-chemical properties, especially the amylose/amylopectin ratio, the degree of branching, the average chain length, the phosphate content, the pastification behavior, the size and/or the shape of the starch granule, the viscuous properties and/or the side chain distribution. There is the possibility of increasing the yield of genetically modified plants by increasing the activity of the proteins of the invention, e.g. by overexpressing the respective nucleic acid molecules or by making mutants available which are no longer subject to cell-specific regulation schemes and/or different temperature-dependencies with respect to their activity. The economic significance of the chance to interfere with the starch synthesis of maize alone is obvious: maize is the world's most important plant with regard to the production of starch. 80% of the starch globally produced each year is derived from maize.

Therefore it is possible to express the nucleic acid molecules of the invention in plant cells in order to increase the activity of the respective starch phosphorylases. Furthermore, the nucleic acid molecules of the invention may be modified by means of methods known to the skilled person, in order to produce starch phosphorylases according to the invention which are no longer subject to the cell-specific regulation mechanisms or show modified temperature-dependencies or substrate or product specificities.

In expressing the nucleic acid molecules of the invention in plants the synthesized proteins may in principle be located in any desired compartment within the plant cell. In order to locate it within a specific compartment, the sequence ensuring the localization in the plastids must be deleted and the remaining coding region optionally has to be linked to DNA sequences which ensure localization in the respective compartment. Such sequences are known (see e.g. Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

Thus, the present invention also relates to transgenic plant cells transformed with a nucleic acid molecule or a vector of the invention, as well as it relates to transgenic plant cells which are derived from cells transformed in such a way. Such cells contain a nucleic acid molecule of the invention which is preferably linked to regulatory DNA elements ensuring the transcription in plant cells, especially with a promoter. Such cells differ from naturally occurring plant cells, e.g. in that they contain a nucleic acid molecule of the invention which does not naturally occur in such cells or in that such a molecule is integrated at some position in the genome of the cell at which it does not naturally occur, i.e. in a different genomic environment. Moreover, such transgenic plant cells of the invention differ from naturally occurring plants among other things in that at least one copy of the nucleic acid molecule of the invention is stably integrated in their genome, possibly in addition to the naturally occurring copies. If the nucleic acid molecule(s) integrated into the cell(s) is/are (an) additional copy (copies) of molecules already occurring naturally in the cells, the plant cells of the invention differ from the naturally occurring plant cells particularly in that this/these additional copy/copies is/are integrated at a location in the genome at which they do not occur naturally. This may be proved, for example, by means of a Southern Blot analysis.

Furthermore, the plant cells of the invention differ from naturally occurring plant cells preferably in at least one of the following features: if the introduced nucleic acid molecule of the invention is heterologous with regard to the plant cell, the transgenic plant cells comprise transcripts of the introduced nucleic acid molecules of the invention. This may be determined, for example, by means of a Northern Blot analysis. The plant cells of the invention preferably contain a protein encoded by an introduced nucleic acid molecule of the invention. This may be determined, for example, by means of immunological methods, in particular by means of a Western Blot analysis.

If the introduced nucleic acid molecule of the invention is homologous with regard to the plant cell, the cells of the invention may be distinguished from naturally occurring cells, for example, by the additional expression of nucleic acid molecules of the invention.

The transgenic plant cells of the invention preferably contain more transcripts of the nucleic acid molecules of the invention. This may be shown, for example, by Northern Blot analysis. Thereby, "more" preferably means at least 10% more, more preferably at least 20% more and particularly preferred at least 50% more transcripts than the corresponding non-transformed cells. Furthermore, the cells preferably comprise a corresponding increase in the amount of the protein of the invention (at least 10%, 20% or, as the case may be, 50%). The transgenic plant cells may be regenerated to whole plants according to methods known to the skilled person.

The plants obtained by regenerating the transgenic plant cells of the invention are also the subject-matter of the present invention. A further subject-matter of the invention are plants which contain the above-described transgenic plant cells. The transgenic plants may in principle be plants of any desired species, i.e. they may be monocotyledonous as well as dicotyledonous plants. These are preferably useful plants, i.e. plants cultivated by man as foodstuffs or for technical, in particular for industrial purposes. They are in particular starch-synthesizing or starch-storing plants such as cereals (rye, barley, oats, wheat, millet, sago etc.), amaranth (Amaranthus), rice, lentil, peas, chick-pea, mung bean, broad bean, scarlet runner bean, cassava, potato, sweet potato, tomato, rape seed, soy bean, hemp, flax, sunflower, cow pea or arrowroot. Maize is particularly preferred.

The invention also relates to propagation material of the plants of the invention, e.g. fruits, seeds, tubers, root-stocks, seedlings, cuttings, calli, protoplasts, cell cultures etc.

The present invention further relates to a method for producing a modified starch comprising the step of extracting the starch from an above-described plant of the invention and/or from starch-storing parts of such a plant. Preferably, such a method also comprises the step of harvesting the cultivated plants and/or starch-storing parts of such plants before extracting the starch. Most preferably, it further comprises the step of cultivating the plants of the invention before harvesting. Methods for the extraction of starch from plants or from starch-storing parts of plants are known to the skilled person. Methods for the extraction of starch from maize seeds have been described e.g. in Eckhoff et al. (Cereal Chem. 73 (1996) 54–57). The extraction of maize starch on an industrial level is usually achieved by the so-called wet-milling technique. Furthermore, methods for the extraction of starch from various other starch-storing plants have been described, e.g. in "Starch: Chemistry and Technology (Editor: Whistler, BeMiller and Paschall (1994), $2^{nd}$ edition, Academic Press Inc. London Ltd; ISBN 0-12-746270-8; see e.g. chapter XII, page 412–468: maize and sorghum starches: production; by Watson; chapter XIII, page 469–479: tapioca, arrowroot and sago starches: production; by Corbishley and Miller; chapter XIV, page 479–490: potato starch: production and use; by Mitch; chapter XV, page 491 to 506: wheat starch: production, modification and use; by Knight and Oson; and chapter XVI, page 507 to 528: rice starch: production and use; by Rohmer and Klem). Appliances generally used for extracting starch from plant material are separators, decanters, hydrocyclones, spray dryers and cyclon driers.

Due to the expression or, as the case may be, additional expression of a nucleic acid molecule of the invention, the transgenic plant cells and plants described in the invention synthesize a starch which compared to starch synthesized in wildtype plants is modified for example in its physico-chemical properties, in particular in the amylose/amylopectin ratio, the degree of branching, the average chain-length, the phosphate-content, the pastification behavior, the size and/or the shape of the starch granule. Compared with wildtype-starch, such starch may be modified in particular with respect to its viscosity and/or the gel formation properties of the glues of this starch.

Thus, also the starch obtainable from transgenic plant cells, plants as well as from the propagation material according to the invention is the subject-matter of the present invention.

By means of the nucleic acid molecules of the invention it is furthermore possible to produce maize plant cells and maize plants in which the activity of a protein of the invention is reduced. This also leads to the synthesis of a starch with modified chemical and/or physical properties when compared to the starch from wildtype plant cells.

Thus, transgenic maize plant cells, in which the activity of a protein according to the invention is reduced when compared to non-transformed cells, are a further subject-matter of the invention.

The production of maize plant cells with a reduced activity of a protein of the invention may for example be achieved by the expression of a corresponding antisense-RNA, of a sense-RNA for achieving a cosupression effect or the expression of a correspondingly constructed ribozyme, which specifically cleaves transcripts encoding one of the proteins of the invention, using the nucleic acid molecules of the invention. In order to reduce the activity of a protein of the invention preferably antisense-RNA is expressed in plant cells.

In order to express an antisense-RNA, on the one hand DNA molecules can be used which comprise the complete sequence encoding a protein of the invention, including possibly existing flanking sequences as well as DNA molecules, which only comprise parts of the coding sequence whereby these parts have to be long enough in order to prompt an antisense-effect within the cells.

Basically, sequences with a minimum length of 15 bp, preferably with a length of 100–500 bp, and for an efficient antisense-inhibition, in particular sequences with a length of more than 500 bp may be used. Generally DNA-molecules are used which are shorter than 5000 bp, preferably sequences with a length of less than 2500 bp.

Use may also be made of DNA sequences which are highly homologous, but not completely identical to the sequences of the DNA molecules of the invention. The minimal homology should be more than about 65%. Preferably, use should be made of sequences with homologies between 95 and 100%.

Alternatively, the reduction of the enzyme activity of the starch phosphorylase in plant cells may also be achieved by means of a cosuppression effect, as indicated above. The method is known to the skilled person and has been described, for example, in Jorgensen (Trends Biotechnol. 8 (1990), 340–344), Niebel et al. (Curr. Top. Microbiol. Immunol. 197 (1995), 91–103), Flavell et al. (Curr. Top. Microbiol. 197 (1995), 43–46), Falaqui and Vaucheret (Plant. Mol. Biol. 29 (1995), 149–159), Vaucheret et al. (Mol. Gen. Genet. 248 (1995), 311–317), de Borne et al. (Mol. Gen. Genet. 243 (1994), 613–621) and other sources.

Thus, a subject matter of the present invention are in particular transgenic maize plant cells (a) comprising a DNA molecule which may lead to the synthesis of an antisense RNA which leads to the reduction of the expression of nucleic acid molecules of the invention; and/or
(b) comprising a DNA molecule which may lead to the synthesis of a cosupression RNA which leads to the reduction of the expression of nucleic acid molecules of the invention; and/or
(c) comprising a DNA molecule which may lead to the synthesis of a ribozyme which specifically cleaves transcripts of nucleic acid molecules of the invention.

The cells of the invention preferably show a reduction in the amount of transcripts encoding a protein of the invention when compared to corresponding non-transformed cells, whereby the reduction is preferably at least 30%, more preferably at least 50%, even more preferably at least 70% and most preferably at least 90%. The amount of transcripts in the cells may, for example, be determined by means of a Northern Blot analysis.

The cells preferably show a corresponding, i.e. at least 30%, 50%, 70% or 90% reduction in the amount of the protein of the invention when compared to non-transformed cells. The amount of proteins may be determined, for example, by means of immunological methods, such as Western Blot analysis.

Maize plants containing the transgenic maize plant cells of the invention are also the subject matter of the invention. The invention also relates to the propagation material of the plants of the invention, in particular to seeds, calli, protoplasts, cell cultures etc.

The present invention further relates to a method for producing a modified starch comprising the step of extracting the starch from an above-described plant of the invention and/or from starch-storing parts of such a plant. Preferably, such a method also comprises the step of harvesting the cultivated plants and/or starch-storing parts of such plants before extracting the starch. Most preferably, it further comprises the step of cultivating the plants of the invention before harvesting.

Starch obtainable from the aforementioned transgenic maize plant cells, maize plants as well as propagation material is a further subject matter of the invention as well as starch obtainable from the above-described method of the invention. Due to the reduction of the activity of a protein of the invention, the transgenic maize plant cells and maize plants synthesize a starch which compared to starch synthesized in wildtype plants is modified, for example, in its physico-chemical properties, in particular in the amylose/amylopectin ratio, the degree of branching, the average chain-length, the phosphate-content, the pastification behavior, the side-chain distribution, the size and/or the shape of the starch granule. Compared with wildtype-starch, such starch may be modified in particular with respect to its viscosity and/or the gel formation properties of the glues of this starch.

The starches of the invention may be modified according to techniques known to the skilled person; in unmodified as well as in modified form they are suitable for the use in foodstuffs and for the use in non-foodstuffs.

Basically, the possibilities of uses of the starch can be subdivided into two major fields. One field comprises the hydrolysis products of starch, essentially glucose and glucans components obtained by enzymatic or chemical processes. They can be used as starting material for further chemical modifications and processes, such as fermentation. In this context, it might be of importance that the hydrolysis process can be carried out simply and inexpensively. Currently, it is carried out substantially enzymatically using amyloglucosidase. It is thinkable that costs might be reduced by using lower amounts of enzymes for hydrolysis due to changes in the starch structure, e.g. increasing the surface of the grain, improved digestibility due to less branching or a steric structure, which limits the accessibility for the used enzymes.

The other field in which the starch is used because of its polymer structure as so-called native starch, can be subdivided into two further areas:

1. Use in foodstuffs Starch is a classic additive for various foodstuffs, in which it essentially serves the purpose of binding aqueous additives and/or causes an increased viscosity or an increased gel formation. Important characteristic properties are flowing and sorption behavior, swelling and pastification temperature, viscosity and thickening performance, solubility of the starch, transparency and paste structure, heat, shear and acid resistance, tendency to retrogradation, capability of film formation, resistance to freezing/thawing, digestibility as well as the capability of complex formation with e.g. inorganic or organic ions. A preferred area of application of native starch is the field of bakery-goods and pasta.
2. Use in non-foodstuffs The other major field of application is the use of starch as an adjuvant in various production processes or as an additive in technical products. The major fields of application for the use of starch as an adjuvant are, first of all, the paper and cardboard industry. In this field, the starch is mainly used for retention (holding back solids), for sizing filler and fine particles, as solidifying substance and for dehydration. In addition, the advantageous properties of starch with regard to stiffness, hardness, sound, grip, gloss, smoothness, tear strength as well as the surfaces are utilized.
2.1 Paper and cardboard industry Within the paper production process, a differentiation can be made between four fields of application, namely surface, coating, mass and spraying. The requirements on starch with regard to surface treatment are essentially a high degree of brightness, corresponding viscosity, high viscosity stability, good film formation as well as low formation of dust. When used in coating the solid content, a corresponding viscosity, a high capability to bind as well as a high pigment affinity play an important role. As an additive to the mass rapid, uniform, loss-free dispersion, high mechanical stability and complete retention in the paper pulp are of importance. When using the starch in spraying, corresponding content of solids, high viscosity as well as high capability to bind are also significant.

2.2 Adhesive industry A major field of application is, for instance, in the adhesive industry, where the fields of application are subdivided into four areas: the use as pure starch glue, the use in starch glues prepared with special chemicals, the use of starch as an additive to synthetic resins and polymer dispersions as well as the use of starches as extenders for synthetic adhesives. 90% of all starch-based adhesives are used in the production of corrugated board, paper sacks and bags, composite materials for paper and aluminum, boxes and wetting glue for envelopes, stamps, etc.

2.3 Textile and textile care industry Another possible use as adjuvant and additive is in the production of textiles and textile care products. Within the textile industry, a differentiation can be made between the following four fields of application: the use of starch as a sizing agent, i.e. as an adjuvant for smoothing and strengthening the burring behavior for the protection against tensile forces active in weaving as well as for the increase of wear resistance during weaving, as an agent for textile improvement mainly after quality-deteriorating pretreatments, such as bleaching, dying, etc., as thickener in the production of dye pastes for the prevention of dye diffusion and as an additive for warping agents for sewing yarns.

2.4 Building industry The fourth area of application of starch is its use as an additive in building materials. One example is the production of gypsum plaster boards, in which the starch mixed in the thin plaster pastifies with the water, diffuses at the surface of the gypsum board and thus binds the cardboard to the board. Other fields of application are admixing it to plaster and mineral fibers. In ready-mixed concrete, starch may be used for the deceleration of the sizing process.

2.5 Ground stabilization Furthermore, the starch is advantageous for the production of means for ground stabilization used for the temporary protection of ground particles against water in artificial earth shifting. According to state-of-the-art knowledge, combination products consisting of starch and polymer emulsions can be considered to have the same erosion- and incrustation-reducing effect as the products used so far; however, they are considerably less expensive.

2.6 Use of starch in plant protectives and fertilizers Another field of application is the use of starch in plant protectives for the modification of the specific properties of these preparations. For instance, starches are used for improving the wetting of plant protectives and fertilizers, for the dosed release of the active ingredients, for the conversion of liquid, volatile and/or odorous active ingredients into microcristalline, stable, deformable substances, for mixing incompatible compositions and for the prolongation of the duration of the effect due to a reduced disintegration.

2.7 Drugs, medicine and cosmetics industry Starch may also be used in the fields of drugs, medicine and in the cosmetics industry. In the pharmaceutical industry, the starch may be used as a binder for tablets or for the dilution of the binder in capsules. Furthermore, starch is suitable as disintegrant for tablets since, upon swallowing, it absorbs fluid and after a short time it swells so much that the active ingredient is released. For qualitative reasons, medicinal flowance and dusting powders are further fields of application. In the field of cosmetics, the starch may for example be used as a carrier of powder additives, such as scents and salicylic acid. A relatively extensive field of application for the starch is toothpaste.

2.8 Starch as an additive in coal and briquettes The use of starch as an additive in coal and briquettes is also thinkable. By adding starch, coal can be quantitatively agglomerated and/or briquetted in high quality, thus preventing premature disintegration of the briquettes. Barbecue coal contains between 4 and 6% added starch, calorated coal between 0.1 and 0.5%. Furthermore, the starch is suitable as a binding agent since adding it to coal and briquette can considerably reduce the emission of toxic substances.

2.9 Processing of ore and coal slurry Furthermore, the starch may be used as a flocculant in the processing of ore and coal slurry.

2.10 Starch as an additive in casting Another field of application is the use as an additive to process materials in casting. For various casting processes cores produced from sands mixed with binding agents are needed. Nowadays, the most commonly used binding agent is bentonite mixed with modified starches, mostly swelling starches.

The purpose of adding starch is increased flow resistance as well as improved binding strength. Moreover, swelling starches may fulfill more prerequisites for the production process, such as dispersability in cold water, rehydratisability, good mixability in sand and high capability of binding water.

2.11 Use of starch in rubber industry In the rubber industry starch may be used for improving the technical and optical quality. Reasons for this are improved surface gloss, grip and appearance. For this purpose, the starch is dispersed on the sticky rubberized surfaces of rubber substances before the cold vulcanization. It may also be used for improving the printability of rubber.

2.12 Production of leather substitutes Another field of application for the modified starch is the production of leather substitutes.

2.13 Starch in synthetic polymers In the plastics market the following fields of application are emerging: the integration of products derived from starch into the processing process (starch is only a filler, there is no direct bond between synthetic polymer and starch) or, alternatively, the integration of products derived from starch into the production of polymers (starch and polymer form a stable bond).

The use of the starch as a pure filler cannot compete with other substances such as talcum. This situation is different when the specific starch properties become effective and the property profile of the end products is thus clearly changed. One example is the use of starch products in the processing of thermoplastic materials, such as polyethylene. Thereby, starch and the synthetic polymer are combined in a ratio of 1:1 by means of coexpression to form a 'master batch', from which various products are produced by means of common techniques using granulated polyethylene. The integration of starch in polyethylene films may cause an increased substance permeability in hollow bodies, improved water vapor permeability, improved antistatic behavior, improved antiblock behavior as well as improved printability with aqueous dyes. Another possibility is the use of the starch in polyurethane foams. Due to the adaptation of starch derivatives as well as due to the optimization of processing techniques, it is possible to specifically control the reaction between synthetic polymers and the starch's hydroxy groups. The results are polyurethane films having the following property profiles due to the use of starch: a reduced coefficient of thermal expansion, decreased shrinking behavior, improved pressure/tension behavior, increased water vapor permeability without a change in water acceptance, reduced flammability and cracking density, no drop off of combustible parts, no halides and reduced aging. Disadvantages that presently still exist are reduced pressure and impact strength.

Product development of film is not the only option. Also solid plastics products, such as pots, plates and bowls can be produced by means of a starch content of more than 50%. Furthermore, the starch/polymer mixtures offer the advantage that they are much easier biodegradable.

Furthermore, due to their extreme capability to bind water, starch graft polymers have gained utmost importance. These are products having a backbone of starch and a side lattice of a synthetic monomer grafted on according to the principle of radical chain mechanism. The starch graft polymers available nowadays are characterized by an improved binding and retaining capability of up to 1000 g water per g starch at a high viscosity. These super absorbers are used mainly in the hygiene field, e.g. in products such as diapers and sheets, as well as in the agricultural sector, e.g. in seed pellets.

What is decisive for the use of the new starch modified by recombinant DNA techniques are, on the one hand, structure, water content, protein content, lipid content, fiber content, ashes/phosphate content, amylose/amylopectin ratio, distribution of the relative molar mass, degree of branching, granule size and shape as well as crystallization, and on the other hand, the properties resulting in the following features: flow and sorption behavior, pastification temperature, viscosity, thickening performance, solubility, paste structure, transparency, heat, shear and acid resistance, tendency to retrogradation, capability of gel formation, resistance to freezing/thawing, capability of complex formation, iodine binding, film formation, adhesive strength, enzyme stability, digestibility and reactivity.

The production of modified starch by genetically operating with a transgenic plant may modify the properties of the starch obtained from the plant in such a way as to render further modifications by means of chemical or physical methods superfluous. On the other hand, the starches modified by means of recombinant DNA techniques might be subjected to further chemical modification, which will result in further improvement of the quality for certain of the above-described fields of application. These chemical modifications are principally known to the person skilled in the art. These are particularly modifications by means of heat treatment acid treatment oxidation and esterification leading to the formation of phosphate, nitrate, sulfate, xanthate, acetate and citrate starches. Other organic acids may also be used for the esterification:

formation of starch ethers starch alkyl ether, O-allyl ether, hydroxylalkyl ether, O-carboxylmethyl ether, N-containing starch ethers, P-containing starch ethers and S-containing starch ethers.

formation of branched starches formation of starch graft polymers.

In order to express the nucleic acid molecules of the invention in sense- or antisense-orientation in plant cells, these are normally linked to regulatory DNA elements which ensure the transcription in plant cells. Such regulatory DNA elements are particularly promoters. Basically any promoter which is active in plant cells may be used for the expression.

The promoter may be selected in such a way that the expression takes place constitutively or in a certain tissue, at a certain point of time of the plant development or at a point of time determined by external circumstances. With respect to the plant the promoter may be homologous or heterologous. Suitable promoters for a constitutive expression are, e.g. the 35S RNA promoter of the Cauliflower Mosaic Virus and the ubiquitin promoter from maize. For a tuber-specific expression in potatoes the patatin gene promoter B33 (Rocha-Sosa et al., EMBO J. 8 (1989), 23–29) can be used. A promoter which ensures expression, only in photosynthetically active tissues is, e.g. the ST-LS1 promoter (Stockhaus et al., Proc. Natl. Acad. Sci. USA 84 (1987), 7943–7947; Stockhaus et al., EMBO J. 8 (1989), 2445–2451). For an endosperm-specific expression the HMG promoter from wheat, the USP promoter, the phaseolin promoter or promoters from zein genes from maize are suitable.

Furthermore, a termination sequence may exist which serves to correctly end the transcription and to add a poly-A-tail to the transcript which is believed to stabilize the transcripts. Such elements are described in the literature (cf. Gielen et al., EMBO J. 8 (1989), 23–29) and can be exchanged as desired.

The present invention provides nucleic acid molecules encoding a new type of starch phosphorylase identified in maize. This allows for the identification of the function of this starch phosphorylase in the starch biosynthesis as well as for the production of genetically modified plants in which the activity of this enzyme is modified. This enables the synthesis of starch with a modified structure and therefore with modified physico-chemical properties in the plants manipulated in such a way.

Principally, the nucleic acid molecules of the invention may also be used in order to produce plants in which the activity of the starch phosphorylase of the invention is elevated or reduced and in which at the same time the activities of other enzymes involved in the starch biosynthesis are modified. Thereby, all kinds of combinations and permutations are thinkable. By modifying the activities of a starch phosphorylase in plants, a synthesis of a starch modified in its structure is brought about. Moreover, nucleic acid molecules encoding a protein of the invention, or corresponding antisense-constructs may be introduced into the plant cells, in which the synthesis of endogenous GBSS I-, SSS- or GBSS II-proteins is already inhibited due to an antisense-effect or a mutation, or in which the synthesis of the branching enzyme is inhibited (as described e.g. in WO92/14827 or in the ae-mutant (Shannon and Garwood, 1984, in Whistler, BeMiller and Paschall, Starch: Chemistry and Technology, Academic Press, London, $2^{nd}$ Edition: 25–86)).

If the inhibition of the synthesis of several enzymes involved in the starch biosynthesis in transformed plants is to be achieved, DNA molecules can be used for transformation, which at the same time contain several regions in antisense-orientation controlled by a suitable promoter and encoding the corresponding enzymes. Hereby, each sequence may be controlled by its own promoter or else the sequences may be transcribed as a fusion from a common promoter. The last alternative will generally be preferred as in this case the synthesis of the respective proteins should be inhibited to approximately the same extent. For the length of the single coding regions used in such a construct the same applies which has already been said above in connection with the production of antisense-constructs. There is no upper limit for the amount of the antisense fragments transcribed by a promoter in such a DNA molecule. The produced transcript, however, should usually not be longer than 10 kb or, preferably, 5 kb.

Coding regions which are localized in such DNA molecules in combination with other coding regions in antisense orientation behind a suitable promoter may be derived from DNA sequences coding for the following proteins: starch granule-bound (GBSS I and II) and soluble starch synthases (SSS I and II), branching enzymes, debranching enzymes and disproportioning enzymes. This enumeration only serves as an example. The use of other DNA sequences is also thinkable within the framework of such a combination.

By means of such constructs it is possible to simultaneously inhibit the synthesis of a number of enzymes in plant cells transformed therewith.

Furthermore, the constructs may be inserted into classical mutants which are deficient for at least one gene of the starch biosynthesis (Shannon and Garwood, 1984, in Whistler, BeMiller and Paschall, Starch: Chemistry and Technology, Academic Press, London, $2^{nd}$ edition: 25–86). These deficiencies may relate to the following proteins: starch granule-bound (GBSS I and II) and soluble starch synthases (SSS I and II), branching enzymes (BE I and II), debranching enzymes (R enzymes), disproportioning enzymes and starch phosphorylases. This enumeration only serves as an example.

By proceeding in such a way it is furthermore possible to simultaneously inhibit the synthesis of a number of enzymes in plant cells transformed therewith.

In order to prepare the introduction of foreign genes into higher plants a multitude of cloning vectors is available comprising a replication signal for E.coli and a marker gene for the selection of transformed bacterial cells. Examples for such vectors are pBR322, pUC series, M13mp series, pACYC184 etc. The desired sequence may be integrated into the vector at a suitable restriction site. The obtained plasmid is preferably used for the transformation of E.coli cells. Transformed E.coli cells are cultivated in a suitable medium and subsequently harvested and lysed. The plasmid is recovered. As an analyzing method for the characterization of the obtained plasmid DNA use is generally made of restriction analyses, gel electrophoreses and other biochemico-molecularbiological methods. After each manipulation the plasmid DNA may be cleaved and the obtained DNA fragments may be linked to other DNA sequences. Each plasmid DNA sequence may be cloned into the same or in other plasmids.

In order to introduce DNA into plant host cells a wide range of techniques are at disposal. These techniques comprise the transformation of plant cells with T-DNA by using Agrobacterium tumefaciens or Agrobacterium rhizogenes as transformation medium, the fusion of protoplasts, the injection and the electroporation of DNA, the integration of DNA by means of the biolistic method as well as further possibilities.

In the case of injection and electroporation of DNA into plant cells, there are no special demands made to the plasmids used. Simple plasmids such as pUC derivatives may be used. However, in case that whole plants are to be regenerated from cells transformed in such a way, a selectable marker gene should be present.

Depending on the method of introducing desired genes into the plant cell, further DNA sequences may be necessary. If the Ti- or Ri-plasmid is used e.g. for the transformation of the plant cell, in general at least the right border, more frequently, however, the right and left border of the Ti- and Ri-plasmid T-DNA should be connected to the foreign gene to be introduced as a flanking region.

If Agrobacteria are used for the transformation, the DNA which is to be introduced should advantageously be cloned into special plasmids, namely either into an intermediate vector or into a binary vector. Due to sequences homologous to the sequences within the T-DNA, the intermediate vectors may be integrated into the Ti- or Ri-plasmid of the Agrobacterium due to homologous recombination. This also contains the vir-region necessary for the transfer of the T-DNA. Intermediate vectors cannot replicate in Agrobacteria. By means of a helper plasmid the intermediate vector may be transferred to Agrobacterium tumefaciens (conjugation). Binary vectors may replicate in E.coli as well as in Agrobacteria. They contain a selectable marker gene as well as a linker or polylinker which is framed by the right and the left T-DNA border region. They may be transformed directly into the Agrobacteria (Holsters et al. Mol. Gen. Genet. 163 (1978), 181–187). The Agrobacterium acting as host cell should contain a plasmid carrying a vir-region. The vir-region is necessary for the transfer of the T-DNA into the plant cell. Additional T-DNA may be present. The Agrobacterium transformed in such a way is used for the transformation of plant cells.

The use of T-DNA for the transformation of plant cells was investigated intensely and described sufficiently in EP 120 516; Hoekema, In: The Binary Plant Vector System Offsetdrukkerij Kanters B. V., Alblasserdam (1985), Chapter V; Fraley et al., Crit. Rev. Plant. Sci., 4, 1–46 and An et al. EMBO J. 4 (1985), 277–287.

For transferring the DNA into the plant cells, plant explants may suitably be co-cultivated with Agrobacterium tumefaciens or Agrobacterium rhizogenes. From the infected plant material (e.g. pieces of leaves, stem segments, roots, but also protoplasts or suspension-cultivated plant cells) whole plants may then be regenerated in a suitable medium which may contain antibiotics or biozides for the selection of transformed cells. The plants obtained in such a way may then be examined as to whether the integrated DNA is present or not. Other possibilities in order to integrate foreign DNA by using the biolistic method or by transforming protoplasts are known to the skilled person (cf. e.g. Willmitzer, L., 1993 Transgenic plants. In: Biotechnology, A Multi-Volume Comprehensive Treatise (H. J. Rehm, G. Reed, A. Pühler, P. Stadler, editors), Vol. 2, 627–659, VCH Weinheim-New York-Basel-Cambridge). Whereas the transformation of dicotyledonous plants by Ti-plasmid-vector systems by means of Agrobacterium tumefaciens is a well-established method, more recent studies indicate that the transformation with vectors based on Agrobacterium can also be used in the case of monocotyledonous plants (Chan et al., Plant Mol. Biol. 22 (1993), 491–506; Hiei et al., Plant J. 6 (1994), 271–282).

Alternative systems for the transformation of monocotyledonous plants are the transformation by means of the biolistic approach, protoplast transformation, electroporation of partially permeablized cells, the introduction of DNA by means of glass fibers.

There are various references in the relevant literature dealing specifically with the transformation of maize (cf. e.g.

WO95/06128, EP 0 513 849; EP 0 465 875). In EP 292 435 a method is described by means of which fertile plants may be obtained starting from mucousless, friable granulous maize callus. In this context it was furthermore observed by Shillito et al. (Bio/Technology 7 (1989), 581) that for regenerating fertile plants it is necessary to start from callus-suspension cultures from which a culture of dividing protoplasts can be produced which is capable to regenerate to plants. After an in vitro cultivation period of 7 to 8 months Shillito et al. obtain plants with viable descendants which, however, exhibited abnormalities in morphology and reproductivity.

Prioli and Söndahl (Bio/Technology 7 (1989), 589) have described how to regenerate and to obtain fertile plants from maize protoplasts of the Cateto maize inbreed Cat 100-1. The authors assume that the regeneration of protoplast to fertile plants depends on a number of various factors such as the genotype, the physiological state of the donor-cell and the cultivation conditions. Once the introduced DNA has been integrated in the genome of the plant cell, it usually continues to be stable there and also remains within the descendants of the originally transformed cell. It usually contains a selectable marker which confers resistance against biozides or against an antibiotic such as kanamycin, G 418, bleomycin, hygromycin or phosphinotricine etc. to the transformed plant cells. The individually selected marker should therefore allow for a selection of transformed cells against cells lacking the introduced DNA.

The transformed cells grow in the usual way within the plant (see also McCormick et al., Plant Cell Reports 5 (1986), 81–84). The resulting plants can be cultivated in the usual way and cross-bred with plants having the same transformed genetic heritage or another genetic heritage. The resulting hybrid individuals have the corresponding phenotypic properties.

Two or more generations should be grown in order to ensure whether the phenotypic feature is kept stably and whether it is transferred. Furthermore, seeds should be harvested in order to ensure that the corresponding phenotype or other properties will remain.

DETAILED DESCRIPTION OF THE INVENTION

Figure 1:
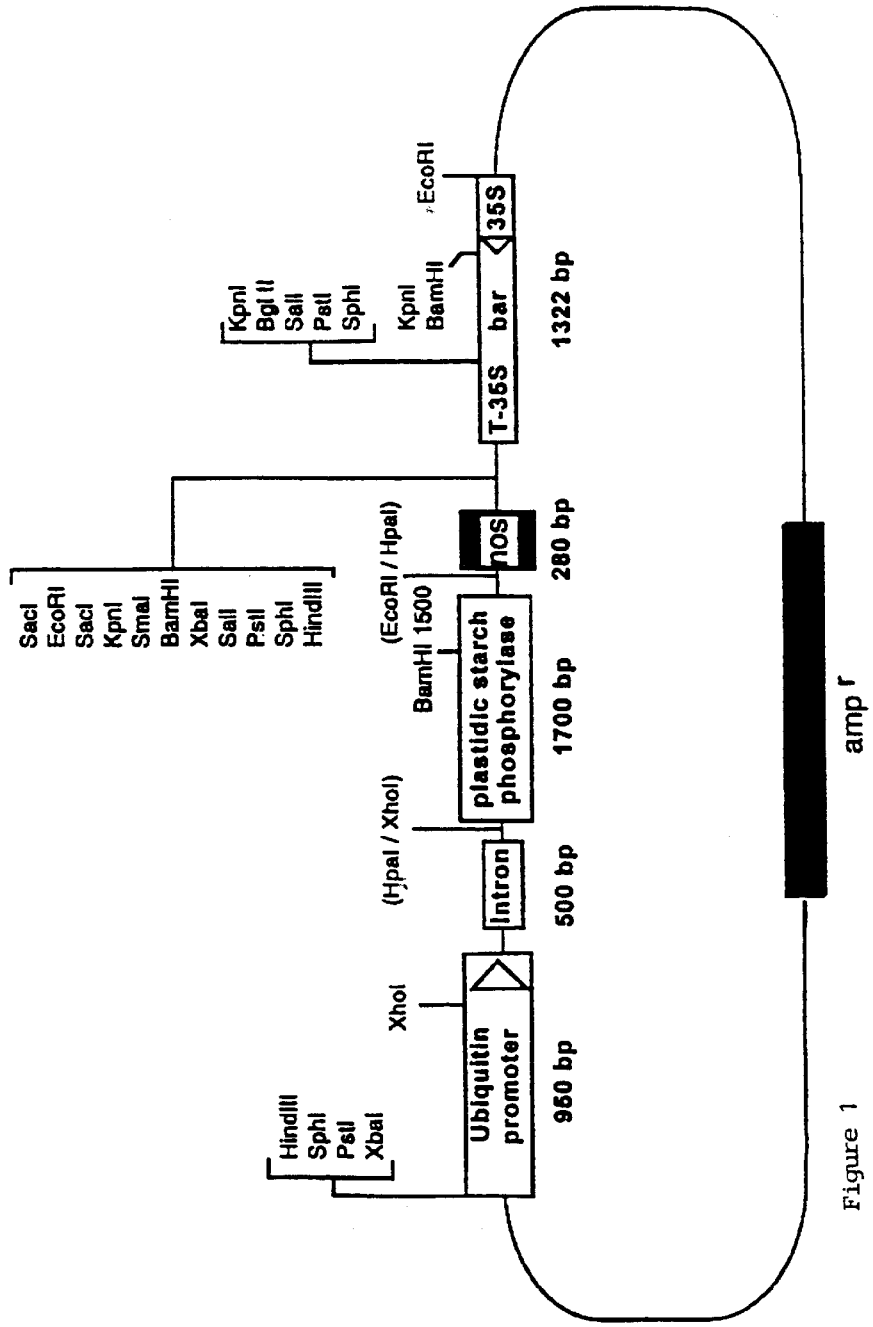
FIG. 1 shows a construct for antisense inhibition of a plastidic isoform of starch phosphorylase in maize.

The examples illustrate the invention.
Media and solutions used in the examples:

| | |
|---|---|
| 20 × SSC: | 175.3 g NaCl |
| | 88.2 g sodium citrate |
| | ad 1000 ml with ddH$_2$O |
| | pH 7.0 with 10 N NaOH |
| YT | 8 g Bacto-Yeast extract |
| | 5 g Bacto-Tryptone |
| | 5 g NaCl |
| | ad 1000 ml with ddH$_2$O |
| Protoplast isolation medium (100 ml) Cellulase Onozuka R S (Meiji Seika, Japan) | 800 mg 2 |
| Pectolyase Y 23 | 40 mg |
| KNO$_3$ | 200 mg |
| KH$_2$PO$_4$ | 136 mg |
| K$_2$HPO$_4$ | 47 mg |

-continued

| | |
|---|---|
| CaCl$_2$ 2H$_2$O | 147 mg |
| MgSO$_4$ 7H$_2$O | 250 mg |
| Bovine serum albumine (BSA) | 20 mg |
| Glucose | 4000 mg |
| Fructose | 4000 mg |
| Sucrose | 1000 mg |
| pH | 5.8 |
| Osmolarity | 660 mosm. |

Protoplast washing solution 1: like protoplast isolating solution, but without cellulase, pectolyase and BSA Transformation buffers:

| | | |
|---|---|---|
| a) | Glucose | 0.5 M |
| | MES | 0.1 % |
| | MgCl$_2$ 6H$_2$O | 25 mM |
| | pH | 5.8 |
| | adjust to 600 mosm. | |
| b) | PEG 6000-solution | |
| | Glucose | 0.5 M |
| | MgCl$_2$ 6H$_2$O | 100 mM |
| | Hepes | 20 mM |
| | pH | 6.5 |

PEG 6000 is added to the buffer described in b) immediately prior to the use of the solution (40% w/v PEG). The solution is filtered with a 0.45 μm sterile filter.

| W5 solution | |
|---|---|
| CaCl$_2$ | 125 mM |
| NaCl | 150 mM |
| KCl | 5 mM |
| Glucose | 50 mM |

Protoplast culture medium (indicated in mg/l)

| | |
|---|---|
| KNO$_3$ | 3000 |
| (NH$_4$)$_2$2SO$_4$ | 500 |
| MgSO$_4$ 7H$_2$O | 350 |
| KH$_2$PO$_4$ | 400 |
| CaCl$_2$ 2H$_2$O | 300 |
| Fe-EDTA and trace elements as in the Murashige-Skoog medium (Physiol. Plant, 15 (1962), 473). | |
| m-inosite | 100 |
| Thiamine HCl | 1.0 |
| Nicotine acid amide | 0.5 |
| Pyridoxine HCl | 0.5 |
| Glycine | 2.0 |
| Glucuronic acid | 750 |
| Galacturonic acid | 750 |
| Galactose | 500 |
| Maltose | 500 |
| Glucose | 36,000 |
| Fructose | 36,000 |
| Sucrose | 30,000 |
| Asparagine | 500 |
| Glutamine | 100 |
| Proline | 300 |
| Caseinhydrolysate | 500 |
| 2,4 dichlorophenoxy acetic acid (2,4-D) | 0.5 |
| pH | 5.8 |
| Osmolarity | 600 mosm. |

In the examples the following methods were used:
1. Cloning methods
   For cloning in *E.coli* the vector pBluescript II SK (Stratagene) was used.

2. Bacterial strains

For the Bluescript vector and for the pUSP constructs use was made of the *E.coli* strain DH5α (Bethesda Research Laboratories, Gaithersburgh, USA). The *E.coli* strain XL1-Blue was used for in vivo excision.

3. Transformation of maize (a) Production of protoplasts of the cell line DSM 6009

Protoplast isolation

2–4 days, preferably 3 days after the last change of medium in a protoplast suspension culture the liquid medium is pumped off and the remaining cells are washed in 50 ml protoplast washing solution 1 and sucked dry once more. 10 ml protoplast isolation medium are added to 2 g of harvested cell mass. The resuspended cells and cell aggregates are incubated at 27±2° C. for 4 to 6 hours in the darkness, while shaking it slightly (at 30 to 40 rpm).

Protoplast purification

As soon as the release of at least 1 million protoplasts/ml has taken place (microscopic inspection), the suspension is sifted through a stainless steel or nylon sieve with a mesh size of 200 or 45 μm. The combination of a 100 μm and a 60 μm sieve allows for separating the cell aggregates just as well. The protoplast-containing filtrate is examined microscopically. It usually contains 98–99% protoplasts. The rest are undigested single cells. Protoplast preparations with such a degree of purity are used for transformation experiments without additional gradient centrifugation. The protoplasts are sedimented by means of centrifugation (100 UpM in the swing-out rotor (100×g, 3 minutes)). The supernatant is abandoned and the protoplasts are resuspended in washing solution 1. The centrifugation is repeated and the protoplasts are subsequently resuspended in the transformation buffer.

(b) Protoplast transformation

The protoplasts resuspended in the transformation buffer are filled in 10 ml portions into 50 ml polyallomer tubes at a titer of $0.5-1\times10^6$ protoplasts/ml. The DNA used for transformation is dissolved in Tris-EDTA (TE) buffer solution. 20 μg plasmid DNA is added to each ml protoplast suspension. A plasmid which provides for resistance to phosphinotricine is used as vector (cf. e.g. EP 0 513 849). After the addition of DNA the protoplast suspension is carefully shaken in order to homogenously distribute the DNA in the solution. Immediately afterwards 5 ml PEG solution is added in drops.

By carefully shaking the tubes the PEG solution is distributed homogenously. Afterwards further 5 ml of PEG solution are added and the homogenous mixing is repeated. The protoplasts remain in the PEG solution for 20 minutes at ±2° C. Afterwards the protoplasts are sedimented by centrifuging for 3 minutes (100 g; 1000 Upm). The supernatant is abandoned. The protoplasts are washed in 20 ml W5 solution by careful shaking and are again subjected to centrifugation. Then they are resuspended in 20 ml protoplast culture medium, centrifuged anew and again resuspended in culture medium. The titer is adjusted to $6-8\times10^5$ protoplasts and the protoplasts are cultivated in 3 ml portions in Petri dishes (Ø 60 mm, height 15 mm). The Petri dishes are sealed with parafilm and stored in darkness at 25±2° C.

(c) Protoplast culture

During the first 2–3 weeks after the protoplast isolation and transformation the protoplasts are cultivated without adding fresh medium. As soon as the cells regenerated from the protoplasts have developed into cell aggregates with more than 20 to 50 cells, 1 ml of fresh protoplast culture medium, containing sucrose as an osmotic (90 g/l), is added.

(d) Selection of transformed maize cells and plant regeneration

3–10 days after adding fresh medium the cell aggregates developed from the protoplasts may be plated on Agar media with 100 mg/l L-phosphinothricine. N6-medium with the vitamins of the protoplast culture medium, 90 g/l sucrose and 1.0 mg/l 2,4D is as suitable as an analogous medium such as a medium with the macro- and micro-nutritive salts of the MS medium (Murashige and Skoog (1962), see above).

The calli developed from stably transformed protoplasts may grow further on the selective medium. After 3 to 5 weeks, preferably 4 weeks the transgenic calli may be transferred to fresh selection medium which also contains 100 mg/l L-phosphinothricine which, however, does no longer contain auxine. Within 3 to 5 weeks approximately 50% of the transgenic maize calli which had integrated the L-phosphinothricine-acetyl-transferase gene into their genome, start to differentiate into plants on this medium in the presence of L-phosphinothricine.

(e) Growing of transgenic regenerative plants

The embryogenical transformed maize tissue is cultivated on hormone-free N6-medium (Chu C. C. et al., Sci. Sin. 16 (1975), 659) in the presence of $5\times10^{-4}$ M L-phosphinothricine. On this medium maize embryos, which express the phosphinothricine-acetyl-transferase gene (PAT gene) in a sufficiently strong manner, develop into plants. Non-transformed embryos or such with only a very weak PAT activity die down. As soon as the leaves of the in-vitro plants have reached a length of 4 to 6 mm, they may be transferred into soil. After washing off the Agar residues at the roots the plants are planted into a mixture of clay, sand, vermiculite and potting soil with the ratio 3:1:1:1 and adapted to the soil culture at 90–100% of relative atmospheric humidity during the first 3 days after planting. The growing is carried out in a climate chamber with a 14 hour light period of approximately 25000 lux at the height of the plant at a day/night temperature of 23±1/17±1° C. The adapted plants are cultivated at an 65±5% atmospheric humidity.

4. Radioactive marking of DNA fragments

The radioactive marking of DNA fragments was carried out by means of a DNA-Random Primer Labeling Kits by Boehringer (Germany) according to the manufacturer's instructions.

EXAMPLE 1

Cloning of a cDNA Encoding a Starch Phosphorylase from *Zea mays*

In order to isolate cDNA molecules encoding a starch phosphorylase from maize, a cDNA library was constructed within the vector Lambda ZAPII (Stratagene) starting from polyA$^+$ RNA from endosperm and packed into phage heads. *E.coli* cells of the XL1 Blue strain were subsequently infected with the phages containing the cDNA fragments (1×10⁶ pfu) and plated on a medium in Petri dishes with a densitiy of approximately 30,000 per 75 cm². After an 8-hour incubation, nitro cellulose membranes were put on the lysated bacterial culture and removed after one minute. The filters were first incubated in 0.2 M NaOH; 1.5 M NaCl for 2 minutes and then in 0.4 M Tris/HCl pH 7.5 for 2 minutes and finally in 2×SSC for 2 minutes. After drying and fixing the DNA by means of UV crosslinking, the filters were incubated in hybridization buffer for 3 hours at 42° C. before a radioactively marked probe was added.

As a probe, use was made of a cDNA from rice encoding a starch phosphorylase from rice (DDBJ accession no. D23280). The hybridization was carried out in 2×SSC, 10×Dehnhardt's solution; 50 mM $Na_2HPO_4$, pH 7.2; 0.2% SDS; 5 mM EDTA and 250 µg/ml denatured herring sperm DNA at 48° C.

Hybridizing phage clones were singled out and further purified by means of standard methods. By means of in vivo excision E.coli clones were derived from positive phage clones. The E.coli clones contained a double-stranded pBluescript plasmid with the respective cDNA insertions. After examining the size and the restriction pattern of the insertion, plasmid DNA was isolated from suitable clones and subsequently sequenced, as described in Example 2.

EXAMPLE 2
Sequence Analysis of the cDNA Insert of the pSTP55 Plasmid

The plasmid pSTP55 was isolated from the E.coli clone which was obtained as described in Example 1, and the sequence of the cDNA insert was determined in a standard routine by means of the didesoxynucleotide-method (Sanger et al., Proc. Natl. Acad. Sci. USA 74 (1977), 5463–5467). The insert has a length of 3320 bp and constitutes a partial cDNA. The nucleotide sequence is indicated under Seq ID No. 1. The corresponding amino acid sequence is indicated under Seq ID No. 2.

A sequence analysis and a comparison with known sequences showed that the sequence shown under Seq ID No. 1 is new and encodes a starch phosphorylase from maize. The probably partial coding region exhibits homology to starch phosphorylases from other organisms, in particular to a starch phosphorylase from rice. Within the framework of this application, the protein encoded by this cDNA insert or by hybridizing sequences is named STP55. By means of this partial cDNA sequence it is possible for the person skilled in the field of molecular biology to isolate the full-length clones comprising the complete coding region and to determine their sequences without any further ado. In order to do so, e.g. a leaf-specific cDNA expression library from Zea mays, line B73 (Stratagene GmbH, Heidelberg) is screened for full-length clones according to standard methods by means of hybridization with a 5'-fragment of the cDNA insert of the pSTP55 plasmid (200 bp). The clones obtained in such are way are subsequently sequenced. On the other hand the missing terminal 5'-sequences may be obtained by using a 5'-Race-method (e.g. of Stratagene or other manufacturers).

Sequence comparisons with cDNA sequences encoding a different plant starch phosphorylase show that the isolated cDNA encodes a type 2 starch phosphorylase.

EXAMPLE 3
Construction of a Vector for Plant Transformation and Generation of Transgenic Maize Plants In order to construct a plant transformation vector which encodes the antisense RNA of the nucleic acid molecule of the invention (starch phosphorylase), the vector pUBIbar (see PCT patent application WO97/44472) was linearized with the restriction enzyme HpaI and dephosphorylated. The linearized vector was then ligated with a blunted 1.7 kb EcoRI/XhoI fragment coding for the starch phosphorylase from maize, obtained from the pBluescript plasmid in Example 1. In order to check the antisense orientation of the ligated cDNA, a restriction analysis was performed which results in the expected 600 bp BamHI fragment.

The plant transformation vector (pUBIbar-αpSTP) is shown in FIG. 1.

The vector was then introduced into maize protoplasts by the above-described method. (100 µg plasmid DNA per 5×10⁷ protoplasts). 350 phosphinotricin-resistant clones were obtained. 70 of these were analyzed. It was found that 20 separate clones contained the DNA encoding the starch phosphorylase in antisense orientation. All of these clones were regenerated to transgenic maize plants.

What is claimed is:

1. An isolated nucleic acid molecule comprising a nucleic acid sequence, wherein the nucleic acid sequence is selected from the group consisting of
   (a) a part of a nucleic acid sequence that has more than 90% overall sequence identity to a nucleic acid sequence encoding a protein comprising the amino acid sequence of SEQ ID NO: 2; and
   (b) a part of a nucleic acid sequence that has more than 90% overall sequence identity to SEQ ID NO: 1;
   wherein the part of the nucleic acid sequence is more than 100 base pairs in length.

2. An isolated nucleic acid molecule comprising a nucleic acid sequence, wherein the nucleic acid sequence is selected from the group consisting of:
   (a) a part of a nucleic acid sequence that has more than 95% overall sequence identity to a nucleic acid sequence encoding a protein comprising the amino acid sequence of SED ID NO: 2;
   (b) a part of a nucleic acid sequence that has more than 95% overall sequence identity SEQ ID NO: 1;
   wherein the part of the nucleic acid sequence is more than 100 base pairs in length.

3. The nucleic acid molecule according to claim 2, wherein the nucleic acid sequence encodes a protein comprising the amino acid sequence of SEQ ID NO: 2.

4. The nucleic acid molecule according to claim 2, wherein the nucleic acid sequence is SEQ ID NO: 1.

5. A nucleic acid construct comprising a regulatory element operably linked to the nucleic acid molecule according to any one of claims 1 or 2–4 wherein the nucleic acid molecule is in antisense orientation with respect to the regulatory element, and wherein the nucleic acid sequence is of sufficient length to reduce the expression of a starch phosphorylase in a plant cell comprising the nucleic acid construct.

6. A vector comprising the nucleic acid construct according to claim 5.

7. A host cell comprising the nucleic acid construct according to claim 5 or comprising a vector comprising said nucleic acid construct.

8. The host cell according to claim 7, wherein the cell is a plant cell.

9. A plant comprising the plant cell according to claim 8.

10. The plant according to claim 9, wherein the expression of the starch phosphorylase is reduced relative to a wild-type plant.

11. The plant according to claim 9, which is a starch-storing plant.

12. The plant according to claim 11, wherein the plant is selected from the group consisting of rye, barley, oats, wheat, rice, maize, pea, cassava and potato.

13. The plant according to claim 12, which is a maize plant.

14. A propagation material of the plant according to claim 9, wherein said propagation material comprises said nucleic acid construct.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 3320 base pairs
      (B) TYPE: nucleic acid
      (C) STRANDEDNESS: single
      (D) TOPOLOGY: linear (ii) MOLECULE TYPE: cDNA to mRNA (iii) HYPOTHETICAL: NO (iv) ANTI-SENSE: NO (vi) ORIGINAL SOURCE:
      (A) ORGANISM: Zea mays

```
              (F) TISSUE TYPE: Endosperm (vii) IMMEDIATE SOURCE:
            (B) CLONE: pSTP55

(ix) FEATURE:
            (A) NAME/KEY: CDS
            (B) LOCATION:1..2949

(xi) SEQUENCE DESCRIPTION: SEQ ID NO: 1:

GGC GAC GAC CAC CTC GCC GCC GCT GCA GCT CGC CAC CGC CTC CCG CCC       48
Gly Asp Asp His Leu Ala Ala Ala Ala Ala Arg His Arg Leu Pro Pro
 1               5                  10                  15

GCA CGC CTC CTC CTC CGG CGG TGG CGG GGT TCT CCT CCG CGG GCG GTT       96
Ala Arg Leu Leu Leu Arg Arg Trp Arg Gly Ser Pro Pro Arg Ala Val
            20                  25                  30

CCG GAG GTG GGG TCG CGC CGG GTC GGG GTC GGG GTC GAG GGG CGA TTG      144
Pro Glu Val Gly Ser Arg Arg Val Gly Val Gly Val Glu Gly Arg Leu
        35                  40                  45

CAG CGG CGG GTG TCG GCG CGC AGC GTG GCG AGC GAT CGG GAC GTG CAA      192
Gln Arg Arg Val Ser Ala Arg Ser Val Ala Ser Asp Arg Asp Val Gln
    50                  55                  60

GGC CCC GTC TCG CCC GCG GAA GGG CTT CCA AAT GTG CTA AAC TCC ATC      240
Gly Pro Val Ser Pro Ala Glu Gly Leu Pro Asn Val Leu Asn Ser Ile
65                  70                  75                  80

GGC TCA TCT GCC ATT GCA TCA AAC ATC AAG CAC CAT GCA GAG TTC GCT      288
Gly Ser Ser Ala Ile Ala Ser Asn Ile Lys His His Ala Glu Phe Ala
                85                  90                  95

CCC TTG TTC TCT CCA GAT CAC TTT TCT CCC CTG AAA GCT TAC CAT GCG      336
Pro Leu Phe Ser Pro Asp His Phe Ser Pro Leu Lys Ala Tyr His Ala
            100                 105                 110

ACT GCT AAA AGT GTC CTT GAT GCG CTG CTG ATA AAC TGG AAT GCG ACA      384
Thr Ala Lys Ser Val Leu Asp Ala Leu Leu Ile Asn Trp Asn Ala Thr
        115                 120                 125

TAT GAT TAT TAC AAC AAA ATG AAT GTA AAA CAA GCA TAT TAC CTG TCC      432
Tyr Asp Tyr Tyr Asn Lys Met Asn Val Lys Gln Ala Tyr Tyr Leu Ser
    130                 135                 140

ATG GAG TTT TTA CAG GGA AGG GCT CTC ACA AAT GCT ATT GGC AAT CTA      480
Met Glu Phe Leu Gln Gly Arg Ala Leu Thr Asn Ala Ile Gly Asn Leu
145                 150                 155                 160

GAG ATT ACT GGT GAA TAT GCA GAA GCA TTA AAA CAA CTT GGA CAA AAC      528
Glu Ile Thr Gly Glu Tyr Ala Glu Ala Leu Lys Gln Leu Gly Gln Asn
                165                 170                 175

CTG GAG GAT GTC GCT AGC CAG GAA CCA GAT GCT GCC CTG GGC AAT GGT      576
Leu Glu Asp Val Ala Ser Gln Glu Pro Asp Ala Ala Leu Gly Asn Gly
            180                 185                 190

GGT TTA GGC CGC CTG GCT TCT TGT TTT TTG GAT TCT TTG GCA ACA TTA      624
Gly Leu Gly Arg Leu Ala Ser Cys Phe Leu Asp Ser Leu Ala Thr Leu
        195                 200                 205

AAT TAT CCA GCA TTG GGA TAT GGA CTT CGC TAT GAA TAT GGC CTC TTT      672
Asn Tyr Pro Ala Leu Gly Tyr Gly Leu Arg Tyr Glu Tyr Gly Leu Phe
    210                 215                 220

AAG CAG ATC ATA ACA AAG GAT GGT CAG GAG GAG ATT GCT GAG AAT TGG      720
Lys Gln Ile Ile Thr Lys Asp Gly Gln Glu Glu Ile Ala Glu Asn Trp
225                 230                 235                 240

CTT GAG ATG GGA TAT CCT TGG GAG GTT GTA AGA AAT GAT GTC TCT TAT      768
Leu Glu Met Gly Tyr Pro Trp Glu Val Val Arg Asn Asp Val Ser Tyr
                245                 250                 255

CCT GTG AAA TTC TAT GGT AAA GTG GTG GAA GGC ACT GAT GGT AGG AAG      816
Pro Val Lys Phe Tyr Gly Lys Val Val Glu Gly Thr Asp Gly Arg Lys
            260                 265                 270
```

-continued

```
CAC TGG ATT GGA GGA GAA AAT ATC AAG GCT GTG GCA CAT GAT GTC CCT          864
His Trp Ile Gly Gly Glu Asn Ile Lys Ala Val Ala His Asp Val Pro
        275                 280                 285

ATT CCT GGC TAC AAA ACT AGA ACT ACC AAT AAT CTG CGT CTT TGG TCA          912
Ile Pro Gly Tyr Lys Thr Arg Thr Thr Asn Asn Leu Arg Leu Trp Ser
    290                 295                 300

ACA ACT GTA CCA GCA CAA GAT TTT GAC TTG GCA GCT TTT AAT TCT GGA          960
Thr Thr Val Pro Ala Gln Asp Phe Asp Leu Ala Ala Phe Asn Ser Gly
305                 310                 315                 320

GAT CAT ACC AAG GCA TAT GAA GCT CAT CTA AAC GCT AAA AAG ATA TGC         1008
Asp His Thr Lys Ala Tyr Glu Ala His Leu Asn Ala Lys Lys Ile Cys
                325                 330                 335

CAC ATA TTG TAT CCT GGG GAT GAA TCA CTA GAG GGG AAA GTT CTC CGC         1056
His Ile Leu Tyr Pro Gly Asp Glu Ser Leu Glu Gly Lys Val Leu Arg
            340                 345                 350

TTG AAG CAA CAA TAT ACA TTG TGT TCA GCC TCA CTA CAG GAC ATC ATT         1104
Leu Lys Gln Gln Tyr Thr Leu Cys Ser Ala Ser Leu Gln Asp Ile Ile
        355                 360                 365

GCT CGT TTT GAG AGT AGA GCT GGC GAG TCT CTC AAC TGG GAG GAC TTC         1152
Ala Arg Phe Glu Ser Arg Ala Gly Glu Ser Leu Asn Trp Glu Asp Phe
    370                 375                 380

CCC TCC AAA GTT GCA GTG CAG ATG AAT GAC ACT CAT CCA ACA CTA TGC         1200
Pro Ser Lys Val Ala Val Gln Met Asn Asp Thr His Pro Thr Leu Cys
385                 390                 395                 400

ATT CCT GAG TTA ATG AGA ATA CTG ATG GAT GTT AAG GGA TTA AGC TGG         1248
Ile Pro Glu Leu Met Arg Ile Leu Met Asp Val Lys Gly Leu Ser Trp
                405                 410                 415

AGT GAG GCA TGG AGT ATT ACA GAA AGA ACC GTG GCA TAC ACT AAC CAT         1296
Ser Glu Ala Trp Ser Ile Thr Glu Arg Thr Val Ala Tyr Thr Asn His
            420                 425                 430

ACA GTG CTT CCT GAA GCT CTA GAG AAG TGG AGC TTG GAC ATA ATG CAG         1344
Thr Val Leu Pro Glu Ala Leu Glu Lys Trp Ser Leu Asp Ile Met Gln
        435                 440                 445

AAA CTT TTA CCT CGA CAT GTT GAG ATA ATA GAA ACA ATT GAT GAA GAG         1392
Lys Leu Leu Pro Arg His Val Glu Ile Ile Glu Thr Ile Asp Glu Glu
    450                 455                 460

CTG ATA AAC AAC ATA GTC TCA AAA TAT GGA ACC ACA GAT ACT GAA CTG         1440
Leu Ile Asn Asn Ile Val Ser Lys Tyr Gly Thr Thr Asp Thr Glu Leu
465                 470                 475                 480

TTG AAA AAG AAG CTG AAA GAG ATG AGA ATT CTG GAT AAT GTT GAC CTT         1488
Leu Lys Lys Lys Leu Lys Glu Met Arg Ile Leu Asp Asn Val Asp Leu
                485                 490                 495

CCA GCT TCC ATT TCC CAA CTA TTT GTT AAA CCC AAA GAC AAA AAG GAA         1536
Pro Ala Ser Ile Ser Gln Leu Phe Val Lys Pro Lys Asp Lys Lys Glu
            500                 505                 510

TCT CCT GCT AAA TCA AAG CAA AAG TTA CTT GTT AAA TCT TTG GAG ACT         1584
Ser Pro Ala Lys Ser Lys Gln Lys Leu Leu Val Lys Ser Leu Glu Thr
        515                 520                 525

ATT GTT GAG GTT GAG GAG AAA ACT GAG TTG GAA GAG GAG GCG GAG GTT         1632
Ile Val Glu Val Glu Glu Lys Thr Glu Leu Glu Glu Glu Ala Glu Val
    530                 535                 540

CTA TCT GAG ATA GAG GAG GAA AAA CTT GAA TCT GAA GAA GTA GAG GCA         1680
Leu Ser Glu Ile Glu Glu Glu Lys Leu Glu Ser Glu Glu Val Glu Ala
545                 550                 555                 560

GAA GAA GCG AGT TCT GAG GAT GAG TTA GAT CCA TTT GTA AAG TCT GAT         1728
Glu Glu Ala Ser Ser Glu Asp Glu Leu Asp Pro Phe Val Lys Ser Asp
                565                 570                 575

CCT AAG TTA CCA AGA GTT GTC CGA ATG GCA AAC CTC TGT GTT GTT GGT         1776
Pro Lys Leu Pro Arg Val Val Arg Met Ala Asn Leu Cys Val Val Gly
            580                 585                 590
```

```
GGG CAT TCA GTA AAT GGT GTA GCT GAA ATT CAC AGT GAA ATT GTG AAA      1824
Gly His Ser Val Asn Gly Val Ala Glu Ile His Ser Glu Ile Val Lys
        595                 600                 605

CAG GAT GTG TTC AAC AGC TTC TAT GAG ATG TGG CCA ACT AAA TTT CAG      1872
Gln Asp Val Phe Asn Ser Phe Tyr Glu Met Trp Pro Thr Lys Phe Gln
        610                 615                 620

AAT AAA ACA AAT GGA GTG ACT CCC AGG CGT TGG ATC CGG TTT TGT AAT      1920
Asn Lys Thr Asn Gly Val Thr Pro Arg Arg Trp Ile Arg Phe Cys Asn
625                 630                 635                 640

CCT GCA TTA AGT GCA TTA ATT TCA AAG TGG ATT GGT TCT GAT GAC TGG      1968
Pro Ala Leu Ser Ala Leu Ile Ser Lys Trp Ile Gly Ser Asp Asp Trp
                645                 650                 655

GTG CTT AAT ACA GAC AAA CTG GCA GAA CTG AAG AAG TTT GCT GAT AAT      2016
Val Leu Asn Thr Asp Lys Leu Ala Glu Leu Lys Lys Phe Ala Asp Asn
        660                 665                 670

GAA GAT CTG CAT TCA GAG TGG CGT GCT GCT AAG AAG GCT AAC AAA ATG      2064
Glu Asp Leu His Ser Glu Trp Arg Ala Ala Lys Lys Ala Asn Lys Met
        675                 680                 685

AAG GTT ATT TCT CTT ATA AGG GAG AAG ACA GGA TAT ATT GTC AGT CCA      2112
Lys Val Ile Ser Leu Ile Arg Glu Lys Thr Gly Tyr Ile Val Ser Pro
        690                 695                 700

GAT GCA ATG TTT GAT GTG CAG GTG AAA AGG ATA CAT GAA TAT AAG CGG      2160
Asp Ala Met Phe Asp Val Gln Val Lys Arg Ile His Glu Tyr Lys Arg
705                 710                 715                 720

CAG CTG CTA AAT ATC CTT GGA ATT GTC TAC CGC TAC AAG AAG ATG AAA      2208
Gln Leu Leu Asn Ile Leu Gly Ile Val Tyr Arg Tyr Lys Lys Met Lys
                725                 730                 735

GAA ATG AGC ACA GAA GAA AGA GCA AAG AGC TTT GTT CCA AGG GTA TGC      2256
Glu Met Ser Thr Glu Glu Arg Ala Lys Ser Phe Val Pro Arg Val Cys
        740                 745                 750

ATA TTC GGT GGG AAA GCA TTT GCC ACA TAT ATA CAG GCA AAA AGG ATC      2304
Ile Phe Gly Gly Lys Ala Phe Ala Thr Tyr Ile Gln Ala Lys Arg Ile
        755                 760                 765

GTT AAA TTT ATT ACA GAT GTG GCA GCT ACC GTG AAC CAT GAT TCA GAC      2352
Val Lys Phe Ile Thr Asp Val Ala Ala Thr Val Asn His Asp Ser Asp
        770                 775                 780

ATT GGA GAT TTG TTG AAG GTC GTA TTT GTT CCA GAC TAT AAT GTT AGT      2400
Ile Gly Asp Leu Leu Lys Val Val Phe Val Pro Asp Tyr Asn Val Ser
785                 790                 795                 800

GTT GCC GAG GCA CTA ATT CCT GCC AGT GAA TTG TCA CAG CAT ATC AGT      2448
Val Ala Glu Ala Leu Ile Pro Ala Ser Glu Leu Ser Gln His Ile Ser
                805                 810                 815

ACT GCT GGA ATG GAA GCT AGT GGG ACC AGT AAC ATG AAG TTT GCA ATG      2496
Thr Ala Gly Met Glu Ala Ser Gly Thr Ser Asn Met Lys Phe Ala Met
        820                 825                 830

AAC GGT TGC ATT CTT ATT GGA ACT TTA GAT GGT GCA AAT GTG GAG ATC      2544
Asn Gly Cys Ile Leu Ile Gly Thr Leu Asp Gly Ala Asn Val Glu Ile
        835                 840                 845

AGA GAG GAG GTT GGA GAA GAA AAC TTT TTC CTT TTT GGT GCA GAG GCA      2592
Arg Glu Glu Val Gly Glu Glu Asn Phe Phe Leu Phe Gly Ala Glu Ala
850                 855                 860

CAT GAA ATT GCT GGT TTG CGG AAA GAA AGA GCC GAG GGA AAG TTT GTG      2640
His Glu Ile Ala Gly Leu Arg Lys Glu Arg Ala Glu Gly Lys Phe Val
865                 870                 875                 880

CCT GAC CCA AGA TTT GAG GAG GTT AAG GAA TTT GTC CGC AGT GGT GTC      2688
Pro Asp Pro Arg Phe Glu Glu Val Lys Glu Phe Val Arg Ser Gly Val
                885                 890                 895

TTT GGG ACT TAC AGC TAT GAT GAA TTG ATG GGG TCT TTG GAA GGA AAT      2736
Phe Gly Thr Tyr Ser Tyr Asp Glu Leu Met Gly Ser Leu Glu Gly Asn
```

-continued

```
                900               905               910
GAA GGT TAC GGA CGT GCA GAT TAT TTC CTT GTT GGC AAG GAC TTC CCC     2784
Glu Gly Tyr Gly Arg Ala Asp Tyr Phe Leu Val Gly Lys Asp Phe Pro
            915                 920                 925

AGC TAT ATT GAA TGC CAA GAA AAA GTT GAT GAG GCG TAC CGA GAT CAG     2832
Ser Tyr Ile Glu Cys Gln Glu Lys Val Asp Glu Ala Tyr Arg Asp Gln
        930                 935                 940

AAG TTA TGG ACA AGG ATG TCT ATC CTC AAC ACG GCT GGC TCA TCC AAG     2880
Lys Leu Trp Thr Arg Met Ser Ile Leu Asn Thr Ala Gly Ser Ser Lys
945                 950                 955                 960

TTC AGC AGC GAT AGG ACG ATT CAT GAG TAC GCC AAG GAT ATC TGG GAT     2928
Phe Ser Ser Asp Arg Thr Ile His Glu Tyr Ala Lys Asp Ile Trp Asp
                965                 970                 975

ATC AGC CCT GCC ATC CTT CCC TAGACCAGGT GGATATCAGG TTCTTTCGCC        2979
Ile Ser Pro Ala Ile Leu Pro
                980

TATATTTCTG TGAACCCTCA GGATCAAGGA ACAGTTGGTG ACGACATTAA TTTGCCTCAG   3039

CCCCTTAGCA GGAAGCGCTG GTCACCTCAG TTTTGTGTAG ACAAAATCTA GGCATCGATA   3099

AATGATGGGA CTATGCATGG TATTTTGGCA GCACTGTTCA GTACCTTGCC TTTTAAATCT   3159

GGTTTTTGGT GTGTGTGTGT GTAAGCTAAT AAATGTCGAG GCAGGATTGT AGGAACACCA   3219

TTGATCATTT GGCTCGCTGG TGAACCTGGT GACGTATGGT GTAATTAGTA GTTGTTTGCC   3279

AAAAAAAAAA AAAAAAAAAA AAAAAAAAAA AAAAAAAAA A                       3320
```

(2) INFORMATION FOR SEQ ID NO: 2:

(i) SEQUENCE CHARACTERISTICS:
        (A) LENGTH: 983 amino acids
        (B) TYPE: amino acid
        (D) TOPOLOGY: linear (ii) MOLECULE TYPE: protein (xi) SEQUENCE DESCRIPTION: SEQ ID NO: 2:

```
Gly Asp Asp His Leu Ala Ala Ala Ala Arg His Arg Leu Pro Pro
 1               5                  10                  15

Ala Arg Leu Leu Leu Arg Arg Trp Arg Gly Ser Pro Arg Ala Val
                20                  25                  30

Pro Glu Val Gly Ser Arg Arg Val Gly Val Gly Val Glu Gly Arg Leu
                35                  40                  45

Gln Arg Arg Val Ser Ala Arg Ser Val Ala Ser Asp Arg Asp Val Gln
                50                  55                  60

Gly Pro Val Ser Pro Ala Glu Gly Leu Pro Asn Val Leu Asn Ser Ile
 65                 70                  75                  80

Gly Ser Ser Ala Ile Ala Ser Asn Ile Lys His His Ala Glu Phe Ala
                    85                  90                  95

Pro Leu Phe Ser Pro Asp His Phe Ser Pro Leu Lys Ala Tyr His Ala
                    100                 105                 110

Thr Ala Lys Ser Val Leu Asp Ala Leu Leu Ile Asn Trp Asn Ala Thr
                    115                 120                 125

Tyr Asp Tyr Tyr Asn Lys Met Asn Val Lys Gln Ala Tyr Tyr Leu Ser
                    130                 135                 140

Met Glu Phe Leu Gln Gly Arg Ala Leu Thr Asn Ala Ile Gly Asn Leu
145                 150                 155                 160

Glu Ile Thr Gly Glu Tyr Ala Glu Ala Leu Lys Gln Leu Gly Gln Asn
                    165                 170                 175
```

```
Leu Glu Asp Val Ala Ser Gln Glu Pro Asp Ala Ala Leu Gly Asn Gly
                180                 185                 190

Gly Leu Gly Arg Leu Ala Ser Cys Phe Leu Asp Ser Leu Ala Thr Leu
            195                 200                 205

Asn Tyr Pro Ala Leu Gly Tyr Gly Leu Arg Tyr Glu Tyr Gly Leu Phe
        210                 215                 220

Lys Gln Ile Ile Thr Lys Asp Gly Gln Glu Ile Ala Glu Asn Trp
225                 230                 235                 240

Leu Glu Met Gly Tyr Pro Trp Glu Val Arg Asn Asp Val Ser Tyr
                245                 250                 255

Pro Val Lys Phe Tyr Gly Lys Val Glu Gly Thr Asp Gly Arg Lys
            260                 265                 270

His Trp Ile Gly Gly Glu Asn Ile Lys Ala Val Ala His Asp Val Pro
        275                 280                 285

Ile Pro Gly Tyr Lys Thr Arg Thr Thr Asn Asn Leu Arg Leu Trp Ser
        290                 295                 300

Thr Thr Val Pro Ala Gln Asp Phe Asp Leu Ala Ala Phe Asn Ser Gly
305                 310                 315                 320

Asp His Thr Lys Ala Tyr Glu Ala His Leu Asn Ala Lys Lys Ile Cys
                325                 330                 335

His Ile Leu Tyr Pro Gly Asp Glu Ser Leu Glu Gly Lys Val Leu Arg
                340                 345                 350

Leu Lys Gln Gln Tyr Thr Leu Cys Ser Ala Ser Leu Gln Asp Ile Ile
            355                 360                 365

Ala Arg Phe Glu Ser Arg Ala Gly Glu Ser Leu Asn Trp Glu Asp Phe
        370                 375                 380

Pro Ser Lys Val Ala Val Gln Met Asn Asp Thr His Pro Thr Leu Cys
385                 390                 395                 400

Ile Pro Glu Leu Met Arg Ile Leu Met Asp Val Lys Gly Leu Ser Trp
                405                 410                 415

Ser Glu Ala Trp Ser Ile Thr Glu Arg Thr Val Ala Tyr Thr Asn His
            420                 425                 430

Thr Val Leu Pro Glu Ala Leu Glu Lys Trp Ser Leu Asp Ile Met Gln
        435                 440                 445

Lys Leu Leu Pro Arg His Val Glu Ile Ile Glu Thr Ile Asp Glu Glu
        450                 455                 460

Leu Ile Asn Asn Ile Val Ser Lys Tyr Gly Thr Thr Asp Thr Glu Leu
465                 470                 475                 480

Leu Lys Lys Lys Leu Lys Glu Met Arg Ile Leu Asp Asn Val Asp Leu
                485                 490                 495

Pro Ala Ser Ile Ser Gln Leu Phe Val Lys Pro Lys Asp Lys Lys Glu
            500                 505                 510

Ser Pro Ala Lys Ser Lys Gln Lys Leu Leu Val Lys Ser Leu Glu Thr
        515                 520                 525

Ile Val Glu Val Glu Glu Lys Thr Glu Leu Glu Glu Glu Ala Glu Val
        530                 535                 540

Leu Ser Glu Ile Glu Glu Glu Lys Leu Glu Ser Glu Glu Val Glu Ala
545                 550                 555                 560

Glu Glu Ala Ser Ser Glu Asp Glu Leu Asp Pro Phe Val Lys Ser Asp
                565                 570                 575

Pro Lys Leu Pro Arg Val Val Arg Met Ala Asn Leu Cys Val Val Gly
            580                 585                 590

Gly His Ser Val Asn Gly Val Ala Glu Ile His Ser Glu Ile Val Lys
```

-continued

```
            595                 600                 605

Gln Asp Val Phe Asn Ser Phe Tyr Glu Met Trp Pro Thr Lys Phe Gln
            610                 615                 620

Asn Lys Thr Asn Gly Val Thr Pro Arg Arg Trp Ile Arg Phe Cys Asn
625                 630                 635                 640

Pro Ala Leu Ser Ala Leu Ile Ser Lys Trp Ile Gly Ser Asp Asp Trp
                    645                 650                 655

Val Leu Asn Thr Asp Lys Leu Ala Glu Leu Lys Lys Phe Ala Asp Asn
                660                 665                 670

Glu Asp Leu His Ser Glu Trp Arg Ala Lys Lys Ala Asn Lys Met
            675                 680                 685

Lys Val Ile Ser Leu Ile Arg Glu Lys Thr Gly Tyr Ile Val Ser Pro
            690                 695                 700

Asp Ala Met Phe Asp Val Gln Val Lys Arg Ile His Glu Tyr Lys Arg
705                 710                 715                 720

Gln Leu Leu Asn Ile Leu Gly Ile Val Tyr Arg Tyr Lys Lys Met Lys
                    725                 730                 735

Glu Met Ser Thr Glu Glu Arg Ala Lys Ser Phe Val Pro Arg Val Cys
                740                 745                 750

Ile Phe Gly Gly Lys Ala Phe Ala Thr Tyr Ile Gln Ala Lys Arg Ile
            755                 760                 765

Val Lys Phe Ile Thr Asp Val Ala Ala Thr Val Asn His Asp Ser Asp
770                 775                 780

Ile Gly Asp Leu Leu Lys Val Val Phe Val Pro Asp Tyr Asn Val Ser
785                 790                 795                 800

Val Ala Glu Ala Leu Ile Pro Ala Ser Glu Leu Ser Gln His Ile Ser
                    805                 810                 815

Thr Ala Gly Met Glu Ala Ser Gly Thr Ser Asn Met Lys Phe Ala Met
                820                 825                 830

Asn Gly Cys Ile Leu Ile Gly Thr Leu Asp Gly Ala Asn Val Glu Ile
            835                 840                 845

Arg Glu Glu Val Gly Glu Glu Asn Phe Phe Leu Phe Gly Ala Glu Ala
            850                 855                 860

His Glu Ile Ala Gly Leu Arg Lys Glu Arg Ala Glu Gly Lys Phe Val
865                 870                 875                 880

Pro Asp Pro Arg Phe Glu Glu Val Lys Glu Phe Val Arg Ser Gly Val
                    885                 890                 895

Phe Gly Thr Tyr Ser Tyr Asp Glu Leu Met Gly Ser Leu Glu Gly Asn
                900                 905                 910

Glu Gly Tyr Gly Arg Ala Asp Tyr Phe Leu Val Gly Lys Asp Phe Pro
            915                 920                 925

Ser Tyr Ile Glu Cys Gln Glu Lys Val Asp Glu Ala Tyr Arg Asp Gln
930                 935                 940

Lys Leu Trp Thr Arg Met Ser Ile Leu Asn Thr Ala Gly Ser Ser Lys
945                 950                 955                 960

Phe Ser Ser Asp Arg Thr Ile His Glu Tyr Ala Lys Asp Ile Trp Asp
                    965                 970                 975

Ile Ser Pro Ala Ile Leu Pro
                980
```